(12) United States Patent
Aftab et al.

(10) Patent No.: US 10,736,886 B2
(45) Date of Patent: Aug. 11, 2020

(54) METHODS OF USING C-MET MODULATORS

(71) Applicant: Exelixis, Inc., Alameda, CA (US)

(72) Inventors: Dana T. Aftab, San Rafael, CA (US); Thomas Mueller, San Francisco, CA (US); Aaron Weitzman, Los Altos Hills, CA (US); Jaymes Holland, Alameda, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 16/251,617

(22) Filed: Jan. 18, 2019

(65) Prior Publication Data

US 2019/0151302 A1 May 23, 2019

Related U.S. Application Data

(63) Continuation of application No. 14/699,683, filed on Apr. 29, 2015, now abandoned, which is a continuation of application No. 13/389,266, filed as application No. PCT/US2010/044749 on Aug. 6, 2010, now abandoned.

(60) Provisional application No. 61/232,382, filed on Aug. 7, 2009.

(51) Int. Cl.
| | | |
|---|---|---|
| *A61K 51/00* | (2006.01) | |
| *A61M 36/14* | (2006.01) | |
| *A61K 31/47* | (2006.01) | |
| *A61K 31/4706* | (2006.01) | |
| *A61K 41/00* | (2020.01) | |
| *A61K 45/06* | (2006.01) | |
| *A61K 31/495* | (2006.01) | |
| *A61K 31/4188* | (2006.01) | |
| *A61N 5/10* | (2006.01) | |
| *A61K 31/015* | (2006.01) | |

(52) U.S. Cl.
CPC .......... *A61K 31/47* (2013.01); *A61K 31/4188* (2013.01); *A61K 31/4706* (2013.01); *A61K 31/495* (2013.01); *A61K 41/00* (2013.01); *A61K 45/06* (2013.01); *A61N 5/10* (2013.01); *A61K 31/015* (2013.01)

(58) Field of Classification Search
None
See application file for complete search history.

(56) References Cited

U.S. PATENT DOCUMENTS

| | | | |
|---|---|---|---|
| 4,808,715 A | 2/1989 | Boyle et al. | |
| 4,829,069 A | 5/1989 | Takahashi et al. | |
| 5,034,393 A | 7/1991 | Hackler et al. | |
| 5,238,951 A | 8/1993 | Sher et al. | |
| 5,480,883 A | 1/1996 | Spada et al. | |
| 5,650,415 A | 7/1997 | Tang et al. | |
| 5,747,498 A | 5/1998 | Schnur et al. | |
| 5,770,599 A | 6/1998 | Gibson | |
| 5,962,458 A | 10/1999 | Lohmann et al. | |
| 6,071,921 A | 6/2000 | Lohmann et al. | |
| 6,103,728 A | 8/2000 | Tang et al. | |
| 6,126,917 A | 10/2000 | Mishani et al. | |
| 6,143,764 A | 11/2000 | Kubo et al. | |
| 6,184,225 B1 | 2/2001 | Thomas et al. | |
| 6,204,267 B1 | 3/2001 | Tang | |
| 6,235,746 B1 | 5/2001 | Davis et al. | |
| 6,288,082 B1 | 9/2001 | Wissner et al. | |
| 6,294,532 B1 | 9/2001 | Thomas et al. | |
| 6,337,335 B1 | 1/2002 | Hutchings et al. | |
| 6,344,455 B1 | 2/2002 | Bridget et al. | |
| 6,344,459 B1 | 2/2002 | Bridget et al. | |
| 6,358,962 B2 | 3/2002 | Uckun et al. | |
| 6,362,336 B1 | 3/2002 | Lohmann et al. | |
| 6,391,874 B1 | 5/2002 | Cockerill et al. | |
| 6,403,580 B1 | 6/2002 | Himmelsbach et al. | |

(Continued)

FOREIGN PATENT DOCUMENTS

| | | |
|---|---|---|
| EP | 1044969 | 10/2000 |
| EP | 1117653 | 7/2001 |

(Continued)

OTHER PUBLICATIONS

Boschelli et al., "Synthesis and Src kinase inhibitory activity of a series of 4-phenylamino-3-quinolinecarbontriles," J Med. Chem., 44 (5): 822-833 (Mar. 1, 2001).

Kubo et al., "Synthesis and structure-activity relationship for new series of 4-phenoxyquinoline derivatives as specific inhibitors of platelet-derived growth factor receptor tyrosine kinase," Bioorg. Med. Chem., 11 (23), 5117-5133 (Nov. 17, 2003).

Lal et al., "Targeting the c-Met Pathway Potentiates Glioblastoma Responses to gemma-Radiation." Clinical Cancer Research, 11:4479-4486, 2005.

(Continued)

*Primary Examiner* — Michael G. Hartley
*Assistant Examiner* — Melissa J Perreira
(74) *Attorney, Agent, or Firm* — Honigman LLP; Heidi M. Berven; Meghan M. Klaric

(57) ABSTRACT

Methods of treating cancer by administering a compound of Formula I,

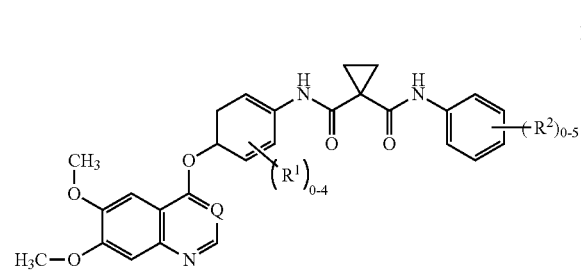

or a pharmaceutically acceptable salt or solvate thereof, in combination with other cancer treatments are described, wherein $R^1$ is halo; $R^2$ is halo; and Q is CH or N.

6 Claims, No Drawings

(56) References Cited

U.S. PATENT DOCUMENTS

| | | |
|---|---|---|
| 6,414,148 B1 | 7/2002 | Thomas et al. |
| 6,432,406 B1 | 8/2002 | Goldberg et al. |
| 6,448,261 B1 | 9/2002 | Bakthavatchalam et al. |
| 6,469,013 B2 | 10/2002 | Uckun et al. |
| 6,472,391 B2 | 10/2002 | Matsumo et al. |
| 6,476,031 B1 | 11/2002 | Chakravarty et al. |
| 6,476,040 B1 | 11/2002 | Norris et al. |
| 6,495,556 B2 | 12/2002 | Uckun et al. |
| 6,514,971 B1 | 2/2003 | Thomas et al. |
| 6,521,618 B2 | 2/2003 | Boschelli et al. |
| 6,521,629 B2 | 2/2003 | Fox et al. |
| 6,525,046 B1 | 2/2003 | Cirillo et al. |
| 6,552,027 B2 | 4/2003 | Uckun et al. |
| 6,562,818 B1 | 5/2003 | Bridges |
| 6,593,333 B1 | 7/2003 | Cumming |
| 6,602,863 B1 | 8/2003 | Bridges et al. |
| 6,608,048 B2 | 8/2003 | Tsou et al. |
| 6,608,071 B2 | 8/2003 | Altmann et al. |
| 6,627,634 B2 | 9/2003 | Hommelsbach et al. |
| 6,630,489 B1 | 10/2003 | Crawley et al. |
| 6,642,242 B2 | 11/2003 | Collis et al. |
| 6,649,620 B2 | 11/2003 | Collis et al. |
| 6,653,305 B2 | 11/2003 | Himmelsbach et al. |
| 6,656,946 B2 | 12/2003 | Himmelsbach et al. |
| 6,664,390 B2 | 12/2003 | Barth et al. |
| 6,673,803 B2 | 1/2004 | Thomas et al. |
| 6,723,726 B1 | 4/2004 | Cockerill et al. |
| 6,727,256 B1 | 4/2004 | Carter et al. |
| 6,734,303 B2 | 5/2004 | Ahman et al. |
| 6,740,651 B2 | 5/2004 | Himmelsbach et al. |
| 6,759,410 B1 | 7/2004 | Adams et al. |
| 6,797,823 B1 | 9/2004 | Kubo et al. |
| 6,809,097 B1 | 10/2004 | Thomas et al. |
| 6,821,987 B2 | 11/2004 | Kubo et al. |
| 7,135,466 B2 | 11/2006 | Sakai et al. |
| 7,253,286 B2 | 8/2007 | Funahashi et al. |
| 7,425,564 B2 | 9/2008 | Fujiwara et al. |
| 7,579,473 B2 | 8/2009 | Bannen et al. |
| 7,598,258 B2 | 10/2009 | Kubo et al. |
| 7,662,783 B2 | 2/2010 | Brooks et al. |
| 7,977,345 B2 | 7/2011 | Bannen et al. |
| 7,999,006 B2 | 8/2011 | Lamb |
| 8,067,436 B2 | 11/2011 | Bannen et al. |
| 8,176,532 B1 | 5/2012 | Bannen et al. |
| 8,314,232 B2 | 11/2012 | Deschamps et al. |
| 8,476,298 B2 | 7/2013 | Bannen et al. |
| 8,497,284 B2 | 7/2013 | Bannen et al. |
| 8,673,912 B2 | 3/2014 | Cannon et al. |
| 8,877,776 B2 * | 11/2014 | Brown .............. C07D 215/22 514/312 |
| 9,174,947 B2 | 11/2015 | Bannen et al. |
| 2002/0032208 A1 | 3/2002 | Lohmann et al. |
| 2002/0049197 A1 | 4/2002 | Himmelsbach et al. |
| 2002/0137757 A1 | 9/2002 | Uckun et al. |
| 2002/0161010 A1 | 10/2002 | Chakravarty et al. |
| 2002/0161226 A1 | 10/2002 | Uckun et al. |
| 2002/0165243 A1 | 11/2002 | Uckun et al. |
| 2002/0169165 A1 | 11/2002 | Kath et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177600 A1 | 11/2002 | Griffin et al. |
| 2002/0177601 A1 | 11/2002 | Himmelsbach et al. |
| 2003/0013728 A1 | 1/2003 | Uckun et al. |
| 2003/0018029 A1 | 1/2003 | Barker et al. |
| 2003/0045525 A1 | 3/2003 | Collis et al. |
| 2003/0045537 A1 | 3/2003 | Lee et al. |
| 2003/0065180 A1 | 4/2003 | Tsou et al. |
| 2003/0066060 A1 | 4/2003 | Ford |
| 2003/0069230 A1 | 4/2003 | Becker et al. |
| 2003/0069248 A1 | 4/2003 | Chakravarty et al. |
| 2003/0082831 A1 | 5/2003 | Fodor et al. |
| 2003/0087907 A1 | 5/2003 | Kubo et al. |
| 2003/0100753 A1 | 5/2003 | Boulton et al. |
| 2003/0149056 A1 | 8/2003 | Wissner et al. |
| 2003/0149062 A1 | 8/2003 | Jung et al. |
| 2003/0153568 A1 | 8/2003 | Kusack et al. |
| 2003/0171386 A1 | 9/2003 | Connell et al. |
| 2003/0176451 A1 | 9/2003 | Carter et al. |
| 2004/0242603 A1 | 12/2004 | Fujiwara et al. |
| 2005/0049264 A1 | 3/2005 | Miwa et al. |
| 2005/0288290 A1 | 12/2005 | Borzilleri et al. |
| 2006/0111375 A1 | 5/2006 | Shumizu et al. |
| 2007/0054928 A1 | 3/2007 | Bannen et al. |
| 2007/0244116 A1 | 10/2007 | Bannen et al. |
| 2008/0004273 A1 | 1/2008 | Raeppel et al. |
| 2008/0161305 A1 | 7/2008 | Forsyth et al. |
| 2008/0207617 A1 | 8/2008 | Miwa et al. |
| 2008/0312221 A1 | 12/2008 | Fujiwara et al. |
| 2009/0170896 A1 | 7/2009 | Bannen et al. |
| 2009/0274693 A1 | 11/2009 | Gilmer et al. |
| 2011/0077233 A1 | 3/2011 | Bannen et al. |
| 2012/0022065 A1 | 1/2012 | Bannen et al. |
| 2012/0035212 A1 | 2/2012 | Bannen et al. |
| 2012/0070368 A1 | 3/2012 | Bannen et al. |
| 2012/0184523 A1 | 7/2012 | Bannen et al. |
| 2012/0252840 A1 | 10/2012 | Aftab et al. |
| 2012/0270872 A1 | 10/2012 | Cannon et al. |
| 2012/0282179 A1 | 11/2012 | Aftab et al. |
| 2013/0030172 A1 | 1/2013 | Wilson et al. |
| 2013/0142790 A1 | 6/2013 | Gilmer et al. |
| 2013/0143881 A1 | 6/2013 | Cannon et al. |
| 2013/0150363 A1 | 6/2013 | Gilmer et al. |
| 2013/0197230 A1 | 8/2013 | Wilson et al. |
| 2013/0252940 A1 | 9/2013 | Bannen et al. |
| 2013/0330377 A1 | 12/2013 | Wilson |
| 2013/0337015 A1 | 12/2013 | Wilson et al. |
| 2014/0155396 A1 | 6/2014 | Bannen et al. |
| 2015/0057310 A1 | 2/2015 | Brown et al. |
| 2015/0202196 A1 | 7/2015 | Bannen et al. |
| 2015/0376133 A1 | 12/2015 | Bannen et al. |
| 2016/0000772 A1 | 1/2016 | Aftab et al. |
| 2016/0185725 A1 | 6/2016 | Bannen et al. |

FOREIGN PATENT DOCUMENTS

| | | |
|---|---|---|
| EP | 1153920 | 11/2001 |
| EP | 0860433 | 7/2002 |
| EP | 1243582 | 9/2002 |
| EP | 0875506 | 2/2003 |
| EP | 0880508 | 4/2003 |
| EP | 1304110 | 4/2003 |
| EP | 0990647 | 7/2003 |
| EP | 912570 | 9/2003 |
| EP | 973746 | 9/2003 |
| EP | 0977737 | 9/2003 |
| EP | 1340748 | 9/2003 |
| EP | 1411046 | 4/2004 |
| EP | 1447405 | 8/2004 |
| EP | 1143950 | 3/2005 |
| EP | 1301440 | 3/2005 |
| WO | 199515758 | 6/1995 |
| WO | 199519774 | 7/1995 |
| WO | 199609294 | 3/1996 |
| WO | 199615118 | 5/1996 |
| WO | 199640142 | 12/1996 |
| WO | 199703069 | 1/1997 |
| WO | 199717329 | 5/1997 |
| WO | 199730035 | 8/1997 |
| WO | 199732856 | 9/1997 |
| WO | 1998002438 | 1/1998 |
| WO | 199813350 | 4/1998 |
| WO | 199813354 | 4/1998 |
| WO | 199910349 | 3/1999 |
| WO | 200018761 | 4/2000 |
| WO | 200020402 | 4/2000 |
| WO | 200021955 | 4/2000 |
| WO | 200043366 | 7/2000 |
| WO | 200047212 | 8/2000 |
| WO | 200055141 | 9/2000 |
| WO | 200056338 | 9/2000 |
| WO | 200056720 | 9/2000 |
| WO | 200068199 | 11/2000 |
| WO | 200068201 | 11/2000 |

(56) References Cited

FOREIGN PATENT DOCUMENTS

| | | |
|---|---|---|
| WO | 200121596 | 3/2001 |
| WO | 200121597 | 3/2001 |
| WO | 200147890 | 7/2001 |
| WO | 200155116 | 8/2001 |
| WO | 2001055116 | 8/2001 |
| WO | 200168186 | 9/2001 |
| WO | 200194341 | 12/2001 |
| WO | 200200188 | 1/2002 |
| WO | 200200649 | 1/2002 |
| WO | 200209684 | 2/2002 |
| WO | 200216352 | 2/2002 |
| WO | 200218351 | 3/2002 |
| WO | 200230924 | 4/2002 |
| WO | 200230926 | 4/2002 |
| WO | 200232872 | 4/2002 |
| WO | 2002032872 | 4/2002 |
| WO | 200234744 | 5/2002 |
| WO | 200236570 | 5/2002 |
| WO | 200244166 | 6/2002 |
| WO | 200285895 | 10/2002 |
| WO | 200288110 | 11/2002 |
| WO | 200292571 | 11/2002 |
| WO | 200292577 | 11/2002 |
| WO | 200292578 | 11/2002 |
| WO | 200292579 | 11/2002 |
| WO | 200296884 | 12/2002 |
| WO | 200300188 | 1/2003 |
| WO | 200300660 | 1/2003 |
| WO | 200333472 | 4/2003 |
| WO | 200340109 | 5/2003 |
| WO | 2003037252 | 5/2003 |
| WO | 200345395 | 6/2003 |
| WO | 200347584 | 6/2003 |
| WO | 200348159 | 6/2003 |
| WO | 2003050108 | 6/2003 |
| WO | 200353960 | 7/2003 |
| WO | 200355491 | 7/2003 |
| WO | 200355492 | 7/2003 |
| WO | 200355866 | 7/2003 |
| WO | 200364413 | 7/2003 |
| WO | 200364421 | 8/2003 |
| WO | 200364431 | 8/2003 |
| WO | 200366060 | 8/2003 |
| WO | 200389439 | 10/2003 |
| WO | 2003082831 | 10/2003 |
| WO | 2003093238 | 11/2003 |
| WO | 200406846 | 1/2004 |
| WO | 200418473 | 4/2004 |
| WO | 2004035572 | 4/2004 |
| WO | 200441829 | 5/2004 |
| WO | 2004039782 | 5/2004 |
| WO | 200454585 | 7/2004 |
| WO | 200455003 | 7/2004 |
| WO | 200458267 | 7/2004 |
| WO | 200460373 | 7/2004 |
| WO | 200503140 | 1/2005 |
| WO | 200505389 | 1/2005 |
| WO | 200530140 | 4/2005 |
| WO | 200573224 | 8/2005 |
| WO | 2006014420 | 2/2006 |
| WO | 2006108059 | 10/2006 |
| WO | 2007064797 | 6/2007 |
| WO | 2007103308 | 9/2007 |
| WO | 2007126799 | 11/2007 |
| WO | 2008035209 | 3/2008 |
| WO | 2009091374 | 7/2009 |
| WO | 2009096435 | 8/2009 |
| WO | 2009136663 | 11/2009 |
| WO | 201039248 | 4/2010 |
| WO | 2010083414 | 7/2010 |

OTHER PUBLICATIONS

Laird et al., "Small molecule tyrosine kinase inhibitors: clinical development of anticancer agents," Expert Opin. Investig. Drugs, 12 (1): 51-64 (Jan. 2003).

Liu, L., et al. "Synergistic Effects of Foretinlb with HER-Targeted Agents in MET and HER1- or HER2-Coactivated Tumor Cells", Molecular Cancer Therapeutics, vol. 10, No. 3, Mar. 1, 2011.

Ogita et al., "Synthesis and structure-activity relationship of diarylamide urea derivatives as selective inhibitors of the proliferation of human coronary artery smooth muscle cells," Bioorg. Med. Chem., 10 (6): 1865-1871 (Jun. 2002).

Riegel et al., "The synthesis of some 4-quinolinols and 4-chloroquinolines by the ethoxymethenemalonic ester method," J Am. Chem. Soc., 68: 1264-1266 (1946).

Schiff et al., Phase 1 does escalation trial of the safety and pharmacokinetics (PK) of cabozantinib (XL184) concurrent with temozolomide (TMZ) & radiation (RT) or TMZ post-RT in newly diagnosed high-grade gliomas (HGG). Presented Nov. 21-24, 2013 at Society for Neuro-Oncology, San Francisco, CA, USA.

Welsh et al., The c-Met receptor tyrosine kinsse inhibitor MP470 radiosensitizes glioblastoma cells., Radiation Oncology, published Dec. 22, 2009, downloaded from http://www.ro-journal.com/content/4/1/69.

DeGroot, et al., "A Phase II Study of XL184 in Patients (pts) with Progressive Glioblastoma Multiforme (GBM) in First or Second Relapse", J. Clin. Oncol. 27:15s, 2009 (suppl; abstr 2047).

Schiff, et al., "Phase 1 Dose Escalation Trial of the Safety and Pharmacokinetics of Cabozantinib Concurrent With Temozolomide and Radiotherapy or Temozolomide After Radiotherapy in Newly Diagnosed Patients with High-Grade Gliomas", Cancer, vol. 122, No. 4, Feb. 15, 2016.

Furuta, Takayuki, "Identification of Potent and Selective Inhibitors of PDGF Receptor Autophosphorylation" Journal of Medicinal Chemistry, vol. 49, No. 7, pp. 2186-2192.

* cited by examiner

METHODS OF USING C-MET MODULATORS

CROSS-REFERENCE TO RELATED APPLICATIONS

This application is a continuation application of U.S. Ser. No. 14/699,683, filed Apr. 29, 2015, which is a continuation of U.S. Ser. No. 13/389,266, filed Jul. 12, 2012, which claims priority under 35 U.S.C. § 371 to Patent Cooperation Treaty application PCT/US2010/044749, filed Aug. 6, 2010, which claims the benefit of U.S. provisional application No. 61/232,382, filed Aug. 7, 2009, the entire contents of which are incorporated herein by reference.

FIELD OF THE INVENTION

This invention relates to methods of using c-Met modulators, and specifically c-Met modulators in combination with other anti-cancer agents and/or radiation, which can be useful for the modulation of various cellular activities and for the treatment of various diseases as described in the specification.

BACKGROUND OF THE INVENTION

Traditionally, dramatic improvements in the treatment of cancer are associated with identification of therapeutic agents acting through novel mechanisms. One mechanism that can be exploited in cancer treatment is the modulation of protein kinase activity because signal transduction through protein kinase activation is responsible for many of the characteristics of tumor cells. Protein kinase signal transduction is of particular relevance in, for example, thyroid, gastric, head and neck, lung, breast, prostate, and colorectal cancers, as well as in the growth and proliferation of brain tumor cells.

Protein kinases can be categorized as receptor type or non-receptor type. Receptor-type tyrosine kinases are comprised of a large number of transmembrane receptors with diverse biological activity. For a detailed discussion of the receptor-type tyrosine kinases, see Plowman et al., DN&P 7(6): 334-339, 1994. Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases, including, for example, immunological disorders, cardiovascular diseases, inflammatory diseases, and degenerative diseases. Therefore, protein kinases are attractive targets for small molecule drug discovery. Particularly attractive targets for small-molecule modulation with respect to antiangiogenic and antiproliferative activity include receptor type tyrosine kinases Ret, c-Met, and VEGFR2.

The kinase c-Met is the prototypic member of a subfamily of heterodimeric receptor tyrosine kinases (RTKs) which include Met, Ron and Sea. The endogenous ligand for c-Met is the hepatocyte growth factor (HGF), a potent inducer of angiogenisis. Binding of HGF to c-Met induces activation of the receptor via autophosphorylation resulting in an increase of receptor dependent signaling, which promotes cell growth and invasion. Anti-HGF antibodies or HGF antagonists have been shown to inhibit tumor metastasis in vivo (See: Maulik et al Cytokine & Growth Factor Reviews 2002 13, 41-59). c-Met, VEGFR2 and/or Ret overexpression has been demonstrated on a wide variety of tumor types including breast, colon, renal, lung, squamous cell myeloid leukemia, hemangiomas, melanomas, astrocytomas, and glioblastomas. The Ret protein is a transmembrane receptor with tyrosine kinase activity. Ret is mutated in most familial forms of medullary thyroid cancer. These mutations activate the kinase function of Ret and covert it into an oncogene product.

Inhibition of EGF, VEGF and ephrin signal transduction will prevent cell proliferation and angiogenesis, two key cellular processes needed for tumor growth and survival (Matter A. Drug Disc. Technol. 2001 6, 1005-1024). Kinase KDR (refers to kinase insert domain receptor tyrosine kinase) and flt-4 (fins-like tyrosine kinase-4) are both vascular endothelial growth factor (VEGF) receptors. Inhibition of EGF, VEGF and ephrin signal transduction will prevent cell proliferation and angiogenesis, two key cellular processes needed for tumor growth and survival (Matter A. Drug Disc. Technol. 2001 6, 1005-1024). EGF and VEGF receptors are desirable targets for small molecule inhibition.

Glioblastoma is the most aggressive form of primary brain tumor, with an incidence of 2.3 per 100,000 persons per year in the United Sates. The median survival time following diagnosis is 12-15 months with current standard of care involving surgery followed by radiation. It has been reported that targeting the MET pathway potentiates GBM response to gamma-radiation (Lal et al, 2005). It has also been report that MET expression correlate with high grade GBM tumors (Hirose et al, 1998) and expression of HGF and MET correlate with malignancy (Koochekpour et al, 1995; Abounader et al, 2001, Uchinokura et al, 2006). It has also been reported that the glioma derived stem cell factor induces angiogenesis within the brain. SCF and VEGF may have complementary roles in the robust angiogenic response in GBM (Sun et al, 2006).

Accordingly, small-molecule compounds that specifically inhibit, regulate and/or modulate the signal transduction of kinases, particularly including Ret, c-Met and VEGFR2 described above, are particularly desirable as a means to treat or prevent disease states associated with abnormal cell proliferation and angiogenesis. One such small-molecule is N-(4-{[6,7-bis(methyloxy)quinolin-4-yl]oxy}phenyl)-N'-(4-fluorophenyl)cyclopropane-1,1-dicarboxamide, which has the chemical structure:

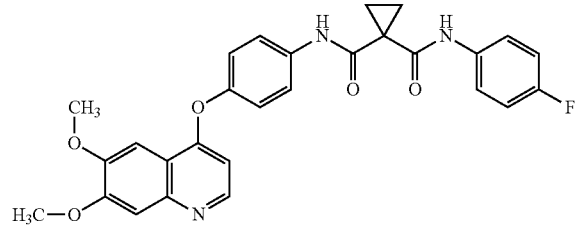 [SMILES: COc1cc2nccc(Oc3ccc(NC(=O)C4(C(=O)Nc5ccc(F)cc5)CC4)cc3)c2cc1OC]

WO 2005/030140 describes the synthesis of N-(4-{[6,7-bis(methyloxy)quinolin-4-yl]oxy}phenyl)-N'-(4-fluorophenyl)cyclopropane-1,1-dicarboxamide (Examples 25, 37, 38, and 48) and also discloses the therapeutic activity of this molecule to inhibit, regulate and/or modulate the signal transduction of kinases, (Assays, Table 4, entry 289). Compound (I) has been measured to have an c-Met $IC_{50}$ value of 1.3 nanomolar (nM) and a Ret $IC_{50}$ value of 5.2 nanomolar (nM).

Thus, finding new uses of compounds for treating diseases by using new combination therapies is desirable.

SUMMARY OF THE INVENTION

The summary of the invention only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

One aspect of this disclosure relates to methods of treating diseases, as defined in the detailed description herein below. These methods of treatment include administering a Compound of Formula I, wherein the compound of Formula I is as define in the detailed description of the invention, to a patient in need of the treatment, in combination with either temozolomide (TMZ) and/or radiation therapy (RT) and optionally one or more additional treatment(s), wherein the one or more additional treatment(s) are as described in the detailed description of the invention.

DETAILED DESCRIPTION OF THE INVENTION

Aspect (I) of this disclosure relates to a method of treating a disease comprising administering to a patient in need of the treatment a compound of Formula I:

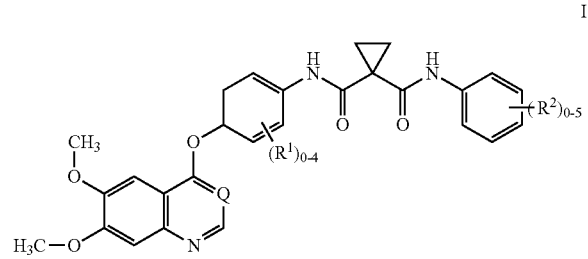

or a pharmaceutically acceptable salt thereof, in combination with temozolomide (TMZ) wherein:
$R^1$ is halo;
$R^2$ is halo; and
Q is CH or N.

Aspect (II) of this disclosure relates to a method of treating a disease comprising administering to a patient in need of the treatment a compound of Formula I:

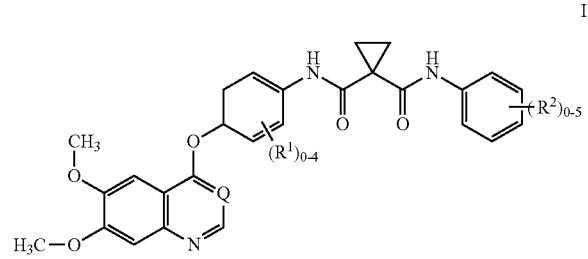

or a pharmaceutically acceptable salt thereof, in combination with radiation therapy (RT) wherein:
$R^1$ is halo;
$R^2$ is halo; and
Q is CH or N.

In other embodiments of aspect (I) and Aspect (II) of this disclosure the compound of Formula I, or a pharmaceutically acceptable salt thereof, is a pharmaceutical composition which further comprises a pharmaceutically acceptable carrier, excipient, or diluent.

In other embodiments of Aspect (I), the method further comprises administering to the patient one or more additional treatment(s), wherein the one or more treatment(s) are selected from (1) surgery, (2) one or more additional chemotherapeutic agent(s), (3) one or more hormone therapy(s), (4) one or more antibody(s), and (5) one or more immunotherapy(ies), (6) radioactive iodine therapy, and (7) radiation.

In other embodiments of Aspect (II), the method further comprises administering to the patient one or more additional treatment(s), wherein the one or more treatment(s) are selected from (1) surgery, (2) one or more additional chemotherapeutic agent(s), (3) one or more hormone therapy(s), (4) one or more antibody(s), and (5) one or more immunotherapy(ies).

In other embodiments of Aspect (I) and Aspect (II), the compound of Formula I in any of the above embodiments is the following compound:

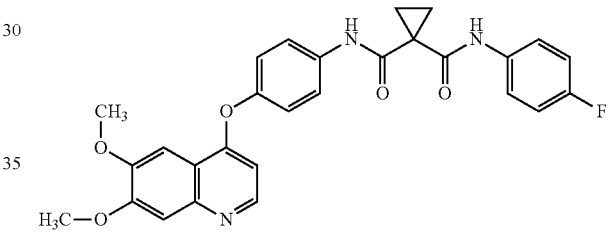

or a pharmaceutical salt thereof.

In other embodiments of Aspect (I) and Aspect (II), the compound of Formula I in any of the above embodiments is the following compound:

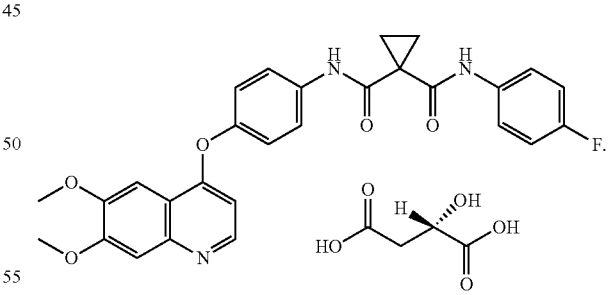

The compound of Formula (I), and all of the embodiments of the compound of Formula (I) as described herein, includes both the recited compounds as well as individual isomers and mixtures of isomers. In each instance, the compound of Formula (I) includes the pharmaceutically acceptable salts, hydrates, and/or solvates of the recited compounds and any individual isomers or mixture of isomers thereof.

Abbreviations and Definitions

The following abbreviations and terms have the indicated meanings throughout:

| Abbreviation | Meaning |
| --- | --- |
| Ac | acetyl |
| Br | broad |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DCM | dichloromethane |
| DME | 1,2-dimethoxyethane |
| DMF | N,N-dimethylformamide |
| DMSO | dimethyl sulfoxide |
| dppf | 1,1'-bis(diphenylphosphano)ferrocene |
| EI | Electron Impact ionization |
| g | gram(s) |
| Gy | Gray unit |
| h or hr | hour(s) |
| HPLC | high pressure liquid chromatography |
| L | liter(s) |
| M | molar or molarity |
| m | Multiplet |
| mg | milligram(s) |
| MGMT | $O^6$-Methylguanine methyltransferase |
| MHz | megahertz (frequency) |
| Min | minute(s) |
| mL | milliliter(s) |
| μL | microliter(s) |
| μM | Micromole(s) or micromolar |
| mM | Millimolar |
| mmol | millimole(s) |
| mol | mole(s) |
| MS | mass spectral analysis |
| N | normal or normality |
| nM | Nanomolar |
| NMR | nuclear magnetic resonance spectroscopy |
| q | Quartet |
| RT | Radiation Therapy |
| s | Singlet |
| t or tr | Triplet |
| TFA | trifluoroacetic acid |
| THF | tetrahydrofuran |
| TLC | thin layer chromatography |

The symbol "—" means a single bond, "═" means a double bond.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

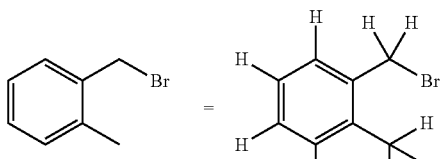

If a group "R" is depicted as "floating" on a ring system, as for example in the formula:

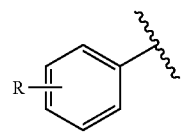

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

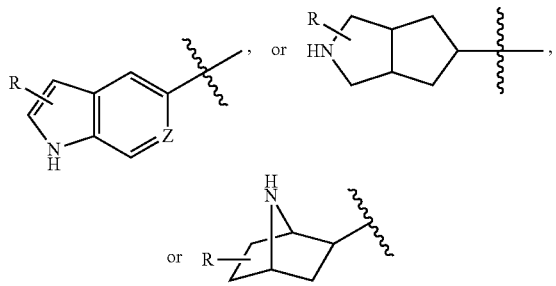

then, unless otherwise defined, a substituent "R" may reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "Z" equals ═CH—) from one of the ring atoms, so long as a stable structure is formed. In the example depicted, the "R" group may reside on either the 5-membered or the 6-membered ring of the fused ring system. In the formulas depicted above, there may more than one R group (R$_y$), wherein y is an integer of 1 or more. When y is 2, for example, then the two "R's" may reside on any two atoms of the ring system, again assuming each replaces a depicted, implied, or expressly defined hydrogen on the ring.

When a group "R" is depicted as existing on a ring system containing saturated carbons, as for example in the formula:

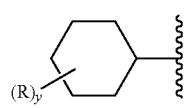

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

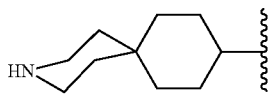

"Halogen" or "halo" refers to fluorine, chlorine, bromine or iodine.

"Yield" for each of the reactions described herein is expressed as a percentage of the theoretical yield.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adeno carcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; and breast cancer. Thus, the term "cancerous cell" as provided herein, includes a cell afflicted by any one of the above-identified conditions.

"Hormone therapy" or "hormonal therapy" includes, for example, treatment with one or more of the following: steroids (e.g. dexamethasone), finasteride, tamoxifen, and an aromatase inhibitor.

"Patient" for the purposes of the present invention includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977;66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Specific salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Platin(s)," and "platin-containing agent(s)" include, for example, cisplatin, carboplatin, and oxaliplatin.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Taxane(s)" includes, for example, one or more of the following: Paclitaxel (Taxol®) and Docetaxel (Taxotere®).

"Therapeutically effective amount" is an amount of a compound of the invention, that when administered to a patient, ameliorates a symptom of the disease. A therapeutically effective amount is intended to include an amount of a compound alone or in combination with other active ingredients effective to modulate Ret, c-Met, and/or VEGFR2, or effective to treat or prevent cancer. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Topoisomerase inhibitor" includes, for example, one or more of the following: amsacrine, camptothecin, etoposide, etoposide phosphate, exatecan, irinotecan, lurtotecan, and teniposide, and topotecan.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

Additional Embodiments of the Invention

In another embodiment of Aspect (I) or Aspect (II) of this disclosure, the disease being treated is selected from astocytoma, glioblastoma, giant cell glioblastoma, gliosarcoma, and glioblastoma with oligodendroglial components.

In another embodiment of Aspect (I) of this disclosure, the method further comprises administering radiation therapy to the patient.

In another embodiment of Aspect (I) of this disclosure, the disease is selected from astocytoma, glioblastoma, giant cell glioblastoma, gliosarcoma, and glioblastoma with oligodendrogilial components; and the method further comprises administering radiation therapy to the patient.

In another embodiment of Aspect (I) or Aspect (II) of this disclosure, the disease is selected from astocytoma, glioblastoma, giant cell glioblastoma, gliosarcoma, and glioblastoma with oligodendrogilial components; and the method further comprises administering surgery to the patient.

In another embodiment of Aspect (I) of this disclosure, the disease is selected from astocytoma, glioblastoma, giant cell glioblastoma, gliosarcoma, and glioblastoma with oligodendrogilial components; and the method further comprises administering radiation therapy and surgery to the patient.

Non-limiting examples of the additional chemotherapeutic agent(s) that can be used in any of the above embodiments include rapamycin, a rapamycin analogue, an alkylating agent(s), a taxane(s), and a platin(s). In chemotherapeutic agent(s) is selected from rapamycin, temozolomide, paclitaxel, docetaxel, carboplatin, cisplatin, oxaliplatin, gefitinib (Iressa®), erlotinib (Tarceva®), Zactima (ZD6474), HKI-272, pelitinib, canertinib, and lapatinib.

A non-limiting example of the antibody that can be used as the one or more additional treatments in Aspect (I) or Aspect (II) of this disclosure is panitumumab.

In another embodiment of Aspect (I) or (II) of this disclosure, the one or more additional treatments is one or more hormone therapy(s). Non-limiting examples of the hormone therapy(s) that can be used in this embodiment include tamoxifen, Toremifene (Fareston), Fulvestrant (Faslodex), Megestrol acetate (Megace), ovarian ablation, Raloxifene, a luteinizing hormone-releasing hormone (LHRH) analog (including goserelin and leuprolide), Megestrol acetate (Megace), and one or more aromatase inhibitor(s); in another embodiment, one or more of the aromatase inhibitor(s) is selected from letrozole (Femara), anastrozole (Arimidex), and exemestane (Aromasin). In another embodiment, one or more of the hormone therapy(s) is selected from tamoxifen and an aromatase inhibitor.

In another embodiment of Aspect (I) or Aspect (II) of this disclosure, the disease is an astrocytic tumor selected from astocytoma, glioblastoma, giant cell glioblastoma, gliosarcoma, and glioblastoma with oligodendroglial components, and the one or more treatment(s) are selected from (1) surgery, (2) radiation, (3) one or more additional chemotherapeutic agent(s), (4) one or more anti-seizure agent(s), and (5) one or more agent(s) to reduce swelling. Non-limiting examples of the radiation treatment that can be used in this embodiment include external beam radiation, interstitial radiotherapy, and stereotactic radiosurgery. Non-limiting examples of the additional chemotherapeutic agent(s)

that can be used in this embodiment include carmustine (BCNU), Erlotinib (Tarceva), bevacizumab, gefitinib (Iressa), rapamycin, cisplatin, BCNU, lomustine, procarbazine, and vincristine. A non-limiting examples of the anti-seizure agent(s) that can be used in this embodiment is diphenylhydantoin (Dilantin). A non-limiting example of the agent that can be used to reduce swelling in this embodiment include dexamethasone (Decadron).

In another embodiment of Aspect (I) of this disclosure, the one or more additional treatments are radiation and surgery.

In another embodiment of Aspect (I) of this disclosure, the one or more additional treatments are radiation and one or more additional chemotherapeutic agent(s).

In another embodiment of Aspect (I) or Aspect (II) of this disclosure, the one or more additional treatments are surgery and one or more additional chemotherapeutic agent(s).

In another embodiment, treatment for patients with GB comprises a (1) "concurrent phase," which is followed by a (2) "rest phase," which is followed by a (3) "maintenance phase."

The concurrent phase is followed by a (2) "rest phase which can range from about 2 weeks to about 8 weeks in duration. The rest phase is meant to allow for recovery from delayed toxicity, if present. In another embodiment, the rest phase can range from about 3 weeks to about 6 weeks in duration. In another embodiment, the rest phase is about 4 weeks in duration.

The rest phase is followed by a (3) "maintenance phase," during which patients receive active pharmaceutical ingredients for approximately twelve 28-day cycles, but can vary from about six to about twenty four 28-day cycles. In various embodiments, patients receive different amounts of the compound of Formula I at different times according to the phase of TMZ and radiation therapy.

Concurrent Phase

During the concurrent phase, the compound of Formula I, in one embodiment, can be administered to the patient concurrently with RT and TMZ for 3-12 weeks, or 4-10 weeks, or 6-7 weeks. In another embodiment, for patients having a mutation in the MGMT promoter wherein the mutated MGMT promoter is an unmethylated promoter, the compound of Formula I will be administered to the patient concurrently with RT for 6-7 weeks in the concurrent phase. The concurrent phase can range from about 3 weeks to about 12 weeks in duration. In another embodiment, the concurrent phase ranges from about 4 weeks to about 10 weeks in duration. In another embodiment, the concurrent phase ranges from about 6 weeks to about 8 weeks in duration. In another embodiment, the concurrent phase ranges from about 6 weeks to about 7 weeks in duration. During the concurrent phase, active pharmaceutical ingredients are given with (RT). In another embodiment, the active pharmaceutical ingredient(s) in the concurrent phase are TMZ and the compound of Formula I. In another embodiment, the active pharmaceutical ingredient in the concurrent phase is TMZ provided that the compound of Formula I is at least one of the active pharmaceutical ingredients in the maintenance phase. In another embodiment, the active pharmaceutical ingredient in the concurrent phase is the compound of Formula I.

Rest Phase

During the rest phase, no RT, compounds of Formula I, or TMZ is administered to the patient. The rest phase can range from about 2 weeks to about 12 weeks. In another embodiment, the rest phase can range from about 3 weeks to about 6 weeks in duration. In another embodiment, the rest phase range is about 4 weeks in duration.

Maintenance Phase

In one embodiment of the maintenance phase, the compound of Formula I is administered to the patient. In another embodiment of the maintenance phase, temozolomide and the compound of Formula I are both administered to the patient. In another embodiment of the maintenance phase, temozolomide and the compound of Formula I are each administered to the patient for a period of time ranging from about 4 months to about 10 months. In another embodiment of the maintenance phase, temozolomide and the compound of Formula I are each administered to the patient for about 4 months. In another embodiment of the maintenance phase, temozolomide and the compound of Formula I are each administered to the patient for about 5 months. In another embodiment of the maintenance phase, temozolomide and the compound of Formula I are each administered to the patient for about 6 months. In another embodiment of the maintenance phase, temozolomide and the compound of Formula I are each administered to the patient for about 7 months. In another embodiment of the maintenance phase, temozolomide and the compound of Formula I are each administered to the patient for about 8 months. In another embodiment of the maintenance phase, temozolomide and the compound of Formula I are each administered to the patient for about 9 months. In another embodiment of the maintenance phase, temozolomide and the compound of Formula I are each administered to the patient for about 10 months. In another embodiment of the maintenance phase, the compound of Formula I is administered to the patient for period of time ranging from about 4 months to about 10 months. In another embodiment of the maintenance phase, the compound of Formula I is administered for about 4 months. In another embodiment of the maintenance phase, the compound of Formula I is administered for about 5 months. In another embodiment of the maintenance phase, the compound of Formula I is administered for about 6 months. In another embodiment of the maintenance phase, the compound of Formula I is administered for about 7 months. In another embodiment of the maintenance phase, the compound of Formula I is administered for about 8 months. In another embodiment of the maintenance phase the compound of Formula I is administered for about 9 months. In another embodiment of the maintenance phase, the compound of Formula I is administered for 10 months.

During the maintenance phase, the compound of Formula I can be administered daily as a single oral agent as a 10-200 mg dosages (which can be in capsules or tablets). In another embodiment of the maintenance phase, the compound of Formula I can be administered daily as a single oral agent as a 25-125 mg dosage, or 25-100 mg dosage, (which can be in a capsule or tablet). Also during the maintenance phase, TMZ can be administered for 5 consecutive days and repeated every 28 days. TMZ, during the maintenance phase, can be administered to the patient as 5-300 mg dosages (which can be in capsules or tablets) to the patient.

For purposes of this disclosure, for all examples that are disclosed herein that refer to the compound of Formula I or temozolomide in dosage amounts in milligrams (mg), it is to be read as mg of the compound in question, and this dosage amount can be administered in any form, including tablet and capsule form. The examples of capsule or tablet forms, that are within the parenthesis after the dosage amounts, are non-limiting examples of how the dosages can be administered and these examples are meant to be non-limiting. For example, in the above embodiment, TMZ can be administered in other modes in addition to capsules or tablets, which are meant to be only non-limiting examples of how the dosage amount can be administered.

In non-limiting examples in all of the above embodiments (including the concurrent and maintenance phases), the compound of Formula I can be administered in 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, and 200 mg dosages (which can be in capsules or tablets).

In non-limiting examples in all of the above embodiments (including the concurrent and maintenance phases), TMZ can be administered in 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 260 mg, 275 mg, 280 mg, 285 mg, 290 mg, 295 mg, and 300 mg dosages (which can be in capsules or tablets).

In another embodiment of Aspect (I) or Aspect (II) of this disclosure, the concurrent phase comprises administering radiation and the compound of Formula I to the patient; the rest phase comprises not administering the compound of Formula I or radiation to the patient; and the maintenance phase comprises administering the compound of Formula I to the patient. In one subembodiment of this embodiment, the concurrent phase can be 7-8 weeks in duration, the rest phase can be about 4 weeks in duration; and the maintenance phase is of a duration sufficient slow down the cancer growth. In another subembodiment of this embodiment, the compound of Formula I is administered to the patient in 25-100 mg dosages, or 25-125 mg dosages, (which can be in capsules or tablets) daily during the concurrent phase; TMZ is administered to the patient in 5-180 mg dosages (which can be in capsules or tablets) daily to the patient during the concurrent phase; RT is administered to the patient during the concurrent phase using 1.8-2 Gy/fraction, daily for 5 days/week for a total dose of up to 60 Gy; the compound of Formula I is administered to the patient in 25-100 mg dosages, or 25-125 mg dosages, (which can be in capsules or tablets) daily during the maintenance phase; and TMZ is administered to the patient in 5-180 mg dosages (which can be in capsules or tablets) for 5 consecutive days and repeated every 28 days until the cancer growth is slowed down.

In other embodiments of any of the above embodiments of Aspect (I) and Aspect (II), the Compound of Formula I is the following compound:

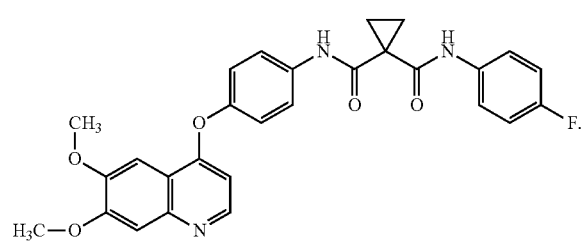 [SMILES: COc1cc2nccc(Oc3ccc(NC(=O)C4(C(=O)Nc5ccc(F)cc5)CC4)cc3)c2cc1OC]

or a pharmaceutical salt thereof.

In another embodiment, the compound of Formula I is the (L)-malate salt form of N-(4-{[6,7-bis(methyloxy)quinolin-4-yl]oxy}phenyl)-N'-(4-fluorophenyl)cyclopropane-1,1-dicarboxamide having the following structure:

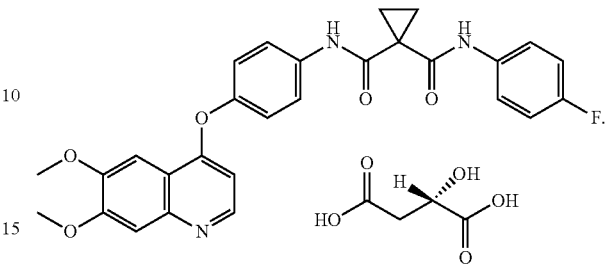

General Administration

In one aspect, the invention provides pharmaceutical compositions comprising a compound of Formula I as described above and a pharmaceutically acceptable carrier, excipient, or diluent. In certain other embodiments, administration is by the oral route. Administration of the compound of Formula I, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin dosages (which can be in capsules or tablets), powders, solutions, suspensions, or aerosols, or the like, specifically in unit dosage forms suitable for simple administration of precise dosages.

The compositions will include a conventional pharmaceutical carrier or excipient and a compound of Formula I as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the compound of Formula I may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the compound of Formula I, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compound of Formula I with, for example, suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of the compound of Formula I include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this dislcosure.

Compressed gases may be used to disperse the compound of Formula I in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of Formula I, or a pharmaceutically acceptable salt thereof, and 99% to 1% by weight of a suitable pharmaceutical excipient. In one example, the composition will be between about 5% and about 75% by weight of a compound(s) of Formula I, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of Formula I, or a pharmaceutically acceptable salt thereof, for treatment of a disease-state in accordance with the teachings of this disclosure.

The compounds of this disclosure, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compound of Formula I can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compound of Formula I within the dosage range described above and the other pharmaceutically active agent (s) within its approved dosage range. Compounds of Formula I may alternatively be used sequentially with known pharmaceutically acceptable agent(s) when a combination formulation is inappropriate.

General Synthesis

Compounds of this invention can be made by the synthetic procedures described below. These procedures are merely illustrative of some methods by which the compounds of Formula I can be synthesized, and various modifications to these procedures can be made. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

The disclosure is further illustrated by the following examples, which are not to be construed as limiting the disclosure in scope or spirit to the specific procedures described in them.

EXAMPLES

Example 1A

Preparation of N-(4-{[6,7-bis(methyloxy)quinolin-4-yl]oxy}phenyl)-N'-(4-fluorophenyl)cyclopropane-1,1-dicarboxamide and the (L)-malate Salt Thereof A synthetic route that has been used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in FIG. 1:

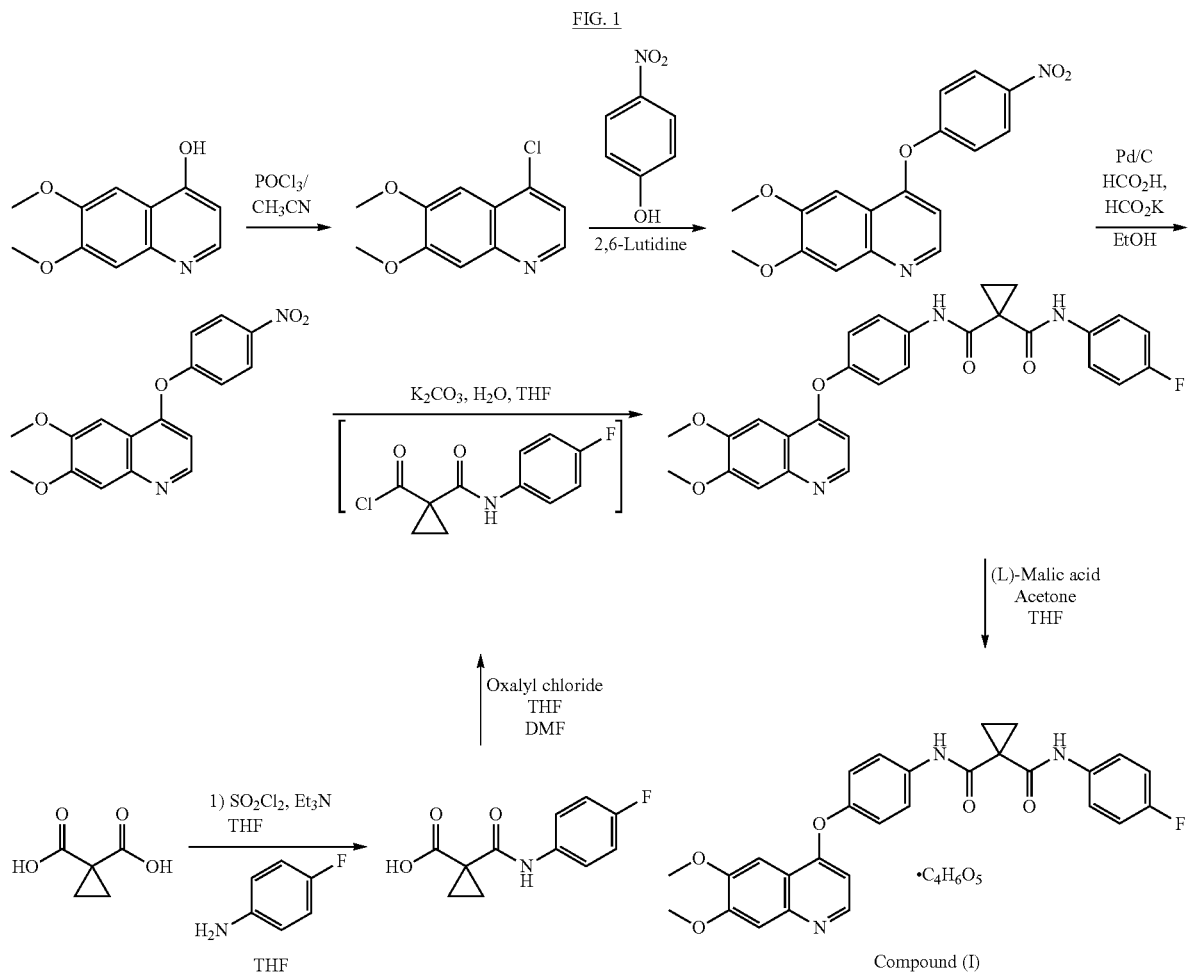

FIG. 1

The process above is described in more detail below.

Preparation of 4-Chloro-6,7-dimethoxy-quinoline

A reactor was charged sequentially with 6,7-dimethoxy-quinoline-4-ol (10.0 kg) and acetonitrile (64.0 L). The resulting mixture was heated to approximately 65° C. and phosphorus oxychloride ($POCl_3$, 50.0 kg) was added. After the addition of $POCl_3$, the temperature of the reaction mixture was raised to approximately 80° C. The reaction was deemed complete (approximately 9.0 hours) when <2% of the starting material remained (in process high-performance liquid chromatography [HPLC] analysis). The reaction mixture was cooled to approximately 10° C. and then quenched into a chilled solution of dichloromethane (DCM, 238.0 kg), 30% $NH_4OH$ (135.0 kg), and ice (440.0 kg). The resulting mixture was warmed to approximately 14° C., and phases were separated. The organic phase was washed with water (40.0 kg) and concentrated by vacuum distillation with the removal of solvent (approximately 190.0 kg). Methyl-t-butyl ether (MTBE, 50.0 kg) was added to the batch, and the mixture was cooled to approximately 10° C., during which time the product crystallized out. The solids were recovered by centrifugation, washed with n heptane (20.0 kg), and dried at approximately 40° C. to afford the title compound (8.0 kg).

Preparation of 6,7-dimethyl-4-(4 nitro-phenoxy)-quinoline

A reactor was sequentially charged with 4-chloro-6,7-dimethoxy-quinoline (8.0 kg), 4 nitrophenol (7.0 kg), 4 dimethylaminopyridine (0.9 kg), and 2,6 lutidine (40.0 kg). The reactor contents were heated to approximately 147° C. When the reaction was complete (<5% starting material remaining as determined by in process HPLC analysis, approximately 20 hours), the reactor contents were allowed to cool to approximately 25° C. Methanol (26.0 kg) was added, followed by potassium carbonate (3.0 kg) dissolved in water (50.0 kg). The reactor contents were stirred for approximately 2 hours. The resulting solid precipitate was filtered, washed with water (67.0 kg), and dried at 25° C. for approximately 12 hours to afford the title compound (4.0 kg).

Preparation of 4-(6,7-dimethoxy-quinoline-4-yloxy)-phenylamine

A solution containing potassium formate (5.0 kg), formic acid (3.0 kg), and water (16.0 kg) was added to a mixture of 6,7-dimethoxy-4-(4 nitro-phenoxy)-quinoline (4.0 kg), 10% palladium on carbon (50% water wet, 0.4 kg) in tetrahydrofuran (40.0 kg) that had been heated to approximately 60° C. The addition was carried out such that the temperature of the reaction mixture remained approximately 60° C. When the reaction was deemed complete as determined using in-process HPLC analysis (<2% starting material remaining, typically 15 hours), the reactor contents were filtered. The filtrate was concentrated by vacuum distillation at approximately 35° C. to half of its original volume, which resulted in the precipitation of the product. The product was recovered by filtration, washed with water (12.0 kg), and dried under vacuum at approximately 50° C. to afford the title compound (3.0 kg).

Preparation of 1-(4-fluoro-phenylcarbamoyl)-cyclopropanecarboxylic acid

Triethylamine (8.0 kg) was added to a cooled (approximately 4° C.) solution of commercially available cyclopropane-1,1-dicarboxylic acid (2.1, 10.0 kg) in THF (63.0 kg) at a rate such that the batch temperature did not exceed 10° C. The solution was stirred for approximately 30 minutes, and then thionyl chloride (9.0 kg) was added, keeping the batch temperature below 10° C. When the addition was complete, a solution of 4-fluoroaniline (9.0 kg) in THF (25.0 kg) was added at a rate such that the batch temperature did not exceed 10° C. The mixture was stirred for approximately 4 hours and then diluted with isopropyl acetate (87.0 kg). This solution was washed sequentially with aqueous sodium hydroxide (2.0 kg dissolved in 50.0 L of water), water (40.0 L), and aqueous sodium chloride (10.0 kg dissolved in 40.0 L of water). The organic solution was concentrated by vacuum distillation followed by the addition of heptane, which resulted in the precipitation of solid. The solid was recovered by centrifugation and then dried at approximately 35° C. under vacuum to afford the title compound. (10.0 kg).

Preparation of 1-(4-Fluoro-phenylcarbamoyl)-cyclopropanecarbonyl chloride

Oxalyl chloride (1.0 kg) was added to a solution of 1-(4-fluoro-phenylcarbamoyl)-cyclopropanecarboxylic acid (2.0 kg) in a mixture of THF (11 kg) and N,N-dimethylformamide (DMF; 0.02 kg) at a rate such that the batch temperature did not exceed 30° C. This solution was used in the next step without further processing.

Preparation of N-(4-{[6,7-bis(methyloxy)quinolin-4-yl]oxy}phenyl)-N'-(4-fluorophenyl)cyclopropane-1, 1-dicarboxamide The solution from the previous step containing 1-(4-fluoro-phenylcarbamoyl)-cyclopropanecarbonyl chloride was added to a mixture of 4-(6,7-dimethoxy-quinoline-4-yloxy)-phenylamine (3.0 kg) and potassium carbonate (4.0 kg) in THF (27.0 kg) and water (13.0 kg) at a rate such that the batch temperature did not exceed 30° C. When the reaction was complete (in typically 10 minutes), water (74.0 kg) was added. The mixture was stirred at 15-30° C. for approximately 10 hours, which resulted in the precipitation of the product. The product was recovered by filtration, washed with a pre made solution of THF (11.0 kg) and water (24.0 kg), and dried at approximately 65° C. under vacuum for approximately 12 hours to afford the title compound (free base, 5.0 kg). $^1$H NMR (400 MHz, $d_6$-DMSO): δ 10.2 (s, 1H), 10.05 (s, 1H), 8.4 (s, 1H), 7.8 (m, 2H), 7.65 (m, 2H), 7.5 (s, 1H), 7.35 (s, 1H), 7.25 (m, 2H), 7.15(m, 2H), 6.4 (s, 1H), 4.0 (d, 6H), 1.5 (s, 4H). LC/MS: M+H=502.

Preparation of N-(4-{[6,7-bis(methyloxy)quinolin-4-yl]oxy}phenyl)-N'-(4-fluorophenyl)cyclopropane-1, 1-dicarboxamide, (L) Malate Salt A solution of L-malic acid (2.0 kg) in water (2.0 kg) was added to a solution of cyclopropane-1,1-dicarboxylic acid [4-(6,7-dimethoxy-quinoline-4-yloxy)-phenyl]-amide (4-fluoro-phenyl)-amide free base (15, 5.0 kg) in ethanol, maintaining a batch temperature of approximately 25° C. Carbon (0.5 kg) and thiol silica (0.1 kg) were then added, and the resulting mixture was heated to approximately 78° C., at which point water (6.0 kg) was added. The reaction mixture was then filtered, followed by the addition of isopropanol (38.0 kg), and was allowed to cool to approximately 25° C. The product was recovered by filtration and washed with isopropanol (20.0 kg) and dried at approximately 65° C. to afford the title compound (5.0 kg).

Example 1B

Preparation of N-(4-{[6,7-bis(methyloxy)quinolin-4-yl]oxy}phenyl)-N'(4-fluorophenyl)cyclopropane-1,1-dicarboxamide and the (L)-malate Salt Thereof Another synthetic route that has been used for the preparation of N-(4-{[6,7-bis(methyloxy)quinolin-4-yl]oxy}phenyl)-N'(4-fluorophenyl)cyclopropane-1,1-dicarboxamide and the (L)-malate salt thereof is depicted in FIG. 2:

mance liquid chromatography [HPLC] analysis). The reaction mixture was cooled to approximately 2-7° C. and then quenched into a chilled solution of dichloromethane (DCM, 482.8 kg), 26% NH$_4$OH (251.3 kg), and water (900 L). The resulting mixture was warmed to approximately 20-25° C., and phases were separated. The organic phase was filtered through a bed of AW hyflo super-cel NF (Celite; 5.4 kg) and the filter bed was washed with DCM (118.9 kg). The combined organic phase was washed with brine (282.9 kg) and mixed with water (120 L). The phases were separated and the organic phase was concentrated by vacuum distillation with the removal of solvent (approximately 95 L residual volume). DCM (686.5 kg) was charged to the

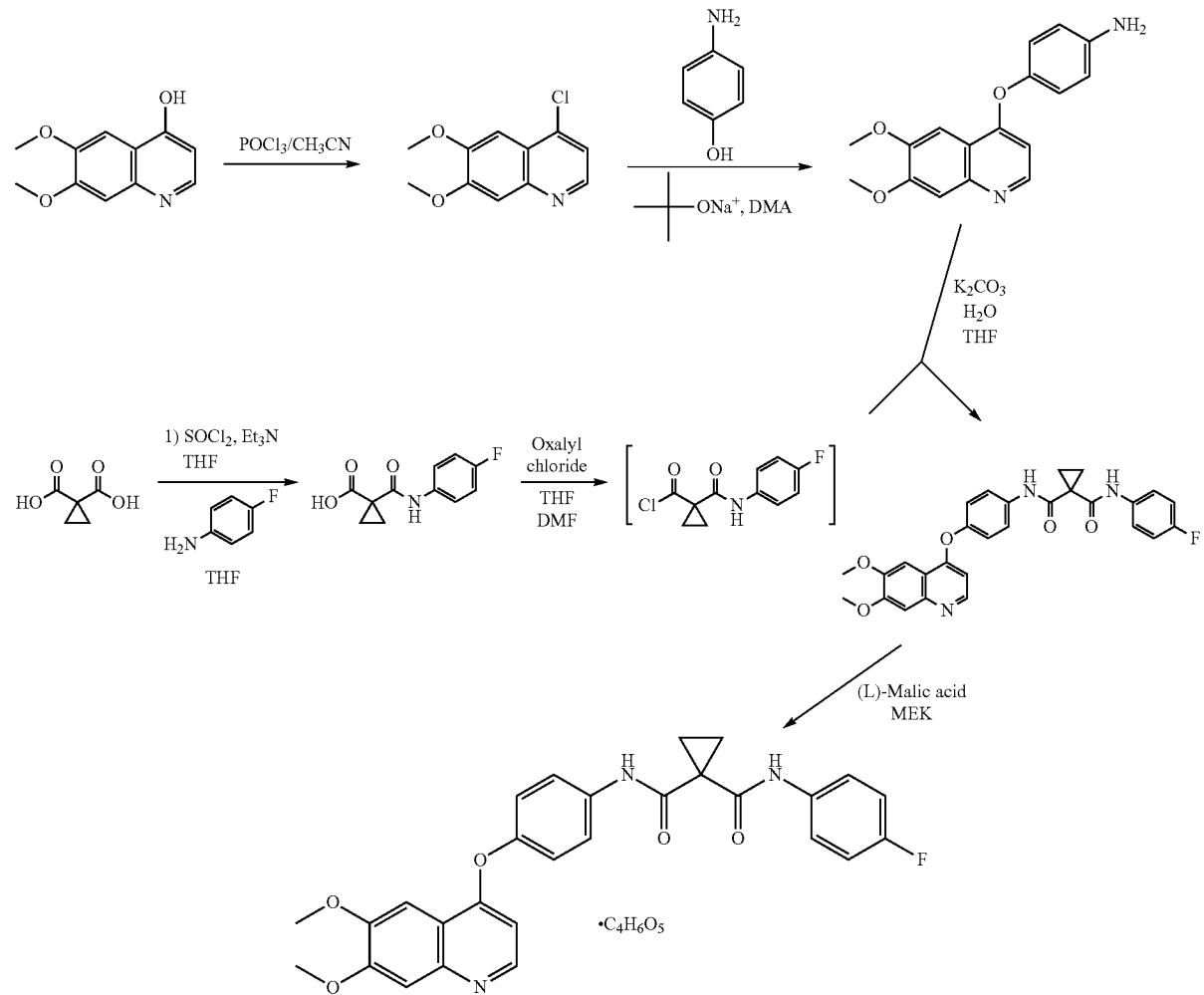

FIG. 2

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C. and phosphorus oxychloride (POCl$_3$, 130.6 kg) was added. After the addition of POCl$_3$, the temperature of the reaction mixture was raised to approximately 77° C. The reaction was deemed complete (approximately 13 hours) when <3% of the starting material remained (in-process high-performance reactor containing organic phase and concentrated by vacuum distillation with the removal of solvent (approximately 90 L residual volume). Methyl t-butyl ether (MTBE, 226.0 kg) was then charged and the temperature of the mixture was adjusted to −20 to −25° C. and held for 2.5 hours resulting in solid precipitate which was then filtered and washed with n-heptane (92.0 kg), and dried on a filter at approximately 25° C. under nitrogen to afford the title compound. (35.6 kg).

Preparation of 4-(6,7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg) and DMA (167.2 kg) at 20-25° C. This mixture was then heated to 100-105° C. for approximately 13 hours. After the reaction was deemed complete as determined using in-process HPLC analysis (<2% starting material remaining), the reactor contents were cooled at 15 to 20° C. and water (pre-cooled, 2 to 7° C., 587 L) charged at a rate to maintain 15 to 30° C. temperature. The resulting solid precipitate was filtered, washed with a mixture of water (47 L) and DMA (89.1 kg) and finally with water (214 L). The filter cake was then dried at approximately 25° C. on filter to yield crude 4-(6,7-dimethoxy-quinoline-4-yloxy)-phenylamine (59.4 kg wet, 41.6 kg dry calculated based on LOD). Crude 4-(6,7-dimethoxy-quinoline-4-yloxy)-phenylamine was refluxed (approximately 75° C.) in a mixture of tetrahydrofuran (THF, 211.4 kg) and DMA (108.8 kg) for approximately 1 h and then cooled to 0-5° C. and aged for approximately 1 h after which time the solid was filtered, washed with THF (147.6 kg) and dried on a filter under vacuum at approximately 25° C. to yield 4-(6,7-dimethoxy-quinoline-4-yloxy)-phenylamine (34.0 kg).

Preparation of 1-(4-Fluoro-phenylcarbamoyl)-cyclopropanecarboxylic acid

Triethylamine (19.5 kg) was added to a cooled (approximately 5 C) solution of cyclopropane-1,1-dicarboxylic acid (24.7 kg) in THF (89.6 kg) at a rate such that the batch temperature did not exceed 5° C. The solution was stirred for approximately 1.3 h, and then thionyl chloride (23.1 kg) was added, keeping the batch temperature below 10 C. When the addition was complete, the solution was stirred for approximately 4 h keeping the temperature below 10° C. A solution of 4-fluoroaniline (18.0 kg) in THF (33.1 kg) was then added at a rate such that the batch temperature did not exceed 10 C. The mixture was stirred for approximately 10 hours after which the reaction was deemed complete. The reaction mixture was then diluted with isopropyl acetate (218.1 kg). This solution was washed sequentially with aqueous sodium hydroxide (10.4 kg, 50% dissolved in 119 L of water) further diluted with water (415 L), then with water (100 L) and finally with aqueous sodium chloride (20.0 kg dissolved in 100 L of water). The organic solution was concentrated by vacuum distillation (100 L residual volume) below 40° C. followed by the addition of n-heptane (171.4 kg), which resulted in the precipitation of solid. The solid was recovered by filtration and washed with n-Heptane (102.4 kg) resulting in wet crude, 1-(4-fluoro-phenylcarbamoyl)-cyclopropanecarboxylic acid (29.0 kg). The crude, 1-(4-fluoro-phenylcarbamoyl)-cyclopropanecarboxylic acid was dissolved in methanol (139.7 kg) at approximately 25° C. followed by the addition of water (320 L) resulting in slurry which was recovered by filtration, washed sequentially with water (20 L) and n-heptane (103.1 kg) and then dried on the filter at approximately 25 C under nitrogen to afford the title compound (25.4 kg).

Preparation of 1-(4-Fluoro-phenylcarbamoyl)-cyclopropanecarbonyl chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25 C. This solution was used in the next step without further processing.

Preparation of cyclopropane-1,1-dicarboxylic acid [4-(6,7-dimethoxy-quinoline-4-yloxy)-phenyl]-amide (4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20-25 C for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45 C under vacuum to afford the title compound (41.0 kg, 38.1 kg, calculated based on LOD).

Preparation of cyclopropane-1,1-dicarboxylic acid [4-(6,7-dimethoxy-quinoline-4-yloxy)-phenyl]-amide (4-fluoro-phenyl)-amide, (L) Malate Salt Cyclopropane-1,1-dicarboxylic acid [4-(6,7-dimethoxy-quinoline-4-yloxy)-phenyl]-amide (4-fluoro-phenyl)-amide (1-5; 13.3 kg), L-malic acid (4.96 kg), methyl ethyl ketone (MEK; 188.6 kg) and water (37.3 kg) were charged to a reactor and the mixture was heated to reflux (approximately 74° C.) for approximately 2 h. The reactor temperature was reduced to 50 to 55° C. and the reactor contents were filtered. These sequential steps described above were repeated two more times starting with similar amounts of 1-5 (13.3 kg), L-Malic acid (4.96 kg), MEK (198.6 kg) and water (37.2 kg). The combined filtrate was azeotropically dried at atmospheric pressure using MEK (1133.2 kg) (approximate residual volume 711 L; KF<0.5% w/w) at approximately 74° C. The temperature of the reactor contents was reduced to 20 to 25° C. and held for approximately 4 hours resulting in solid precipitate which was filtered, washed with MEK (448 kg) and dried under vacuum at 50° C. to afford the title compound (45.5 kg).

Example 2

Administration of the Compound of N-(4-{[6,7-bis(methyloxy)quinolin-4-yl]oxy}phenyl)-N'-(4-fluorophenyl)cyclopropane-1,1-dicarboxamide During the Concurrent Phase to Patients Example 2A: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). The concurrent phase is followed by a rest phase that will last for about 4 weeks. TMZ, when given, is supplied as 5, 20, 100, 250, 140 and 180 mg dosages (which can be in capsules or tablets). In another embodiment, the starting dose of TMZ is 75 mg/m$^2$/day with concurrent RT for 6 weeks. For purposes of this patent application, the term "m$^2$" refers to body surface area in patients measured in square meters. Patients receive RT consisting of fractional focal irradiation administered using a 1.8-2 Gy/fraction, daily for 5 days/week for 6-7 weeks, for a total dose of up to 60 Gy.

Example 2B: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg dosages (which can be in capsules or tablets). The concurrent phase is followed by a rest phase that will last for about 4 weeks. TMZ, when given, is supplied as 5 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2C: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 50 mg dosages (which can be in capsules or tablets). The concurrent phase is followed by a rest phase that will last for about 4 weeks. TMZ, when given, is supplied as 5 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2D: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 75 mg dosages (which can be in capsules or tablets). The concurrent phase is followed by a rest phase that will last for about 4 weeks. TMZ, when given, is supplied as 5 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2E: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). The concurrent phase is followed by a rest phase that will last for about 4 weeks. TMZ, when given, is supplied as 5 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2F: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 100 mg dosages (which can be in capsules or tablets). The concurrent phase is followed by a rest phase that will last for about 4 weeks. TMZ, when given, is supplied as 20 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2G: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 50 mg dosages (which can be in capsules or tablets). The concurrent phase is followed by a rest phase that will last for about 4 weeks. TMZ, when given, is supplied as 20 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2H: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4- yl]oxy}phenyl)-N-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 75 mg dosages (which can be in capsules or tablets). The concurrent phase is followed by a rest phase that will last for about 4 weeks. TMZ, when given, is supplied as 20 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2I: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). The concurrent phase is followed by a rest phase that will last for about 4 weeks. TMZ, when given, is supplied as 20 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2J: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 100 mg dosages (which can be in capsules or tablets). The concurrent phase is followed by a rest phase that will last for about 4 weeks. TMZ, when given, is supplied as 20 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2K: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg dosages (which can be in capsules or tablets). The concurrent phase is followed by a rest phase that will last for about 4 weeks. TMZ, when given, is supplied as 100 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2L: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 50 mg dosages (which can be in capsules or tablets). The concurrent phase is followed by a rest phase that will last for about 4 weeks. TMZ, when given, is supplied as 100 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2M: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 75 mg dosages (which can be in capsules or tablets). The concurrent phase is followed by a rest phase that will last for about 4 weeks. TMZ, when given, is supplied as 100 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2N: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). The concurrent phase is followed by a rest phase that will last for about 4 weeks. TMZ, when given, is supplied as 100 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2O: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4- yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 100 mg dosages (which can be in capsules or tablets). The concurrent phase is followed by a rest phase that will last for about 4 weeks. TMZ, when given, is supplied as 100 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2P: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg dosages (which can be in capsules or tablets). The concurrent phase is followed by a rest phase that will last for about 4 weeks. TMZ, when given, is supplied as 140 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2Q: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 50 mg dosages (which can be in capsules or tablets). The concurrent phase is followed by a rest phase that will last for about 4 weeks. TMZ, when given, is supplied as 140 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2R: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 75 mg dosages (which can be in capsules or tablets). The concurrent phase is followed by a rest phase that will last for about 4 weeks. TMZ, when given, is supplied as 140 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2S: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). The concurrent phase is followed by a rest phase that will last for about 4 weeks. TMZ, when given, is supplied as 140 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2T: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 100 mg dosages (which can be in capsules or tablets). The concurrent phase is followed by a rest phase that will last for about 4 weeks. TMZ, when given, is supplied as 140 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2U: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'(4-fluorophenyl)cyclopropane-1,1-dicarboxamide is administered as a single oral agent supplied as 25 mg dosages (which can be in capsules or tablets). The concurrent phase is followed by a rest phase that will last for about 4 weeks. TMZ, when given, is supplied as 180 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2V: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4- yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 50 mg dosages (which can be in capsules or tablets). The concurrent phase is followed by a rest phase that will last for about 4 weeks. TMZ, when given, is supplied as 180 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2W: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 75 mg dosages (which can be in capsules or tablets). The concurrent phase is followed by a rest phase that will last for about 4 weeks. TMZ, when given, is supplied as 180 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2X: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). The concurrent phase is followed by a rest phase that will last for about 4 weeks. TMZ, when given, is supplied as 180 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2Y: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 100 mg dosages (which can be in capsules or tablets). The concurrent phase is followed by a rest phase that will last for about 4 weeks. TMZ, when given, is supplied as 180 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2Z: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg dosages (which can be in capsules or tablets). The concurrent phase is followed by a rest phase that will last for about 4 weeks. TMZ, when given, is supplied as 250 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2AA: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 50 mg dosages (which can be in capsules or tablets). The concurrent phase is followed by a rest phase that will last for about 4 weeks. TMZ, when given, is supplied as 250 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2AB: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 75 mg dosages (which can be in capsules or tablets). The concurrent phase is followed by a rest phase that will last for about 4 weeks. TMZ, when given, is supplied as 250 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2AC: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4- yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N-(4-fluorophenyl)cyclopropane-1,1-dicarboxamide is administered as a single oral agent supplied as 25 mg and 100 mg dosages (which can be in capsules or tablets). The concurrent phase is followed by a rest phase that will last for about 4 weeks. TMZ, when given, is supplied as 250 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 2AD: N-(4-{[6,7-bis(methyloxy)quinolin-4-yl]oxy}phenyl)-N'-(4-fluorophenyl)cyclopropane-1,1-dicarboxamide is initiated at the start of a 6-7 week concurrent phase of RT and TMZ. Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 100 mg dosages (which can be in capsules or tablets). The concurrent phase is followed by a rest phase that will last for about 4 weeks. TMZ, when given, is supplied as 250 mg dosages (which can be in capsules or tablets). Patients receive RT consisting of fractional focal irradiation administered using a 1.8-2 Gy/fraction, daily for 5 days/week for 6-7 weeks, for a total dose of up to 60 Gy.

Example 3

Administration of the Compound of N-(4-{[6,7-bis(methyloxy)quinolin-4-yl]oxy}phenyl)-N'-(4-fluorophenyl)cyclopropane-1,1-dicarboxamide During the Concurrent Phase to Patients Example 3A: N-(4-{[6,7-bis(methyloxy)quinolin-4-yl]oxy}phenyl)-N'-(4-fluorophenyl)cyclopropane-1,1-dicarboxamide is administered as 25 mg and 100 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 5, 20, 100, 250, 140, 180, and 200 mg dosages (which can be in capsules or tablets) given for 5 consecutive days and repeated every 28 days. In another embodiment, TMZ is administered in the amount of 200 mg/m$^2$/day given for 5 consecutive days and repeated every 28 days. For purposes of this disclosure, the term m2 is meant to mean body surface area in patients measured in square meters. The maintenance phase in Example 3A can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3B: N-(4-{[6,7-bis(methyloxy)quinolin-4-yl]oxy}phenyl)-N'-(4-fluorophenyl)cyclopropane-1,1-dicarboxamide is administered as 25 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 5 mg dosages (which can be in capsules or tablets) given for 5 consecutive days and repeated every 28 days. The maintenance phase in Example 3B can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3C: N-(4-{[6,7-bis(methyloxy)quinolin-4-yl]oxy}phenyl)-N'-(4-fluorophenyl)cyclopropane-1,1-dicarboxamide is administered as 50 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 5 mg dosages (which can be in capsules or tablets) given for 5 consecutive days and repeated every 28 days. The maintenance phase in Example 3C can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3D: N-(4-{[6,7-bis(methyloxy)quinolin-4-yl]oxy}phenyl)-N'-(4-fluorophenyl)cyclopropane-1,1-dicarboxamide is administered as 75 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 5 mg dosages (which can be in capsules or tablets) given for 5 consecutive days and repeated every 28 days. The maintenance phase in Example 3D can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3E: N-(4-{[6,7-bis(methyloxy)quinolin-4-yl]oxy}phenyl)-N'-(4-fluorophenyl)cyclopropane-1,1-dicarboxamide is administered as 100 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4- fluorophenyl)cyclopropane-1,1-dicarboxamide is administered as a single oral agent supplied as 25 mg and 100 mg dosages (which can be in capsules or tablets). TMZ, when given, is supplied as 5 mg dosages (which can be in capsules or tablets) given for 5 consecutive days and repeated every 28 days. The maintenance phase in Example 3E can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3F: N-(4-{[6,7-bis(methyloxy)quinolin-4-yl]oxy}phenyl)-N'-(4-fluorophenyl)cyclopropane-1,1-dicarboxamide is administered as 25 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 20 mg dosages (which can be in capsules or tablets) given for 5 consecutive days and repeated every 28 days. The maintenance phase in Example 3F can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3G: N-(4-{[6,7-bis(methyloxy)quinolin-4-yl]oxy}phenyl)-N'-(4-fluorophenyl)cyclopropane-1,1-dicarboxamide is administered as 50 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 20 mg dosages (which can be in capsules or tablets) given for 5 consecutive days and repeated every 28 days. The maintenance phase in Example 3G can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 82AD.

Example 3H: N-(4-{[6,7-bis(methyloxy)quinolin-4-yl]oxy}phenyl)-N'-(4-fluorophenyl)cyclopropane-1,1-dicarboxamide is administered as 75 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 20 mg dosages (which can be in capsules or tablets) given for 5 consecutive days and repeated every 28 days. The maintenance phase in Example 3H can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3I: N-(4-{[6,7-bis(methyloxy)quinolin-4-yl]oxy}phenyl)-N'-(4-fluorophenyl)cyclopropane-1,1-dicarboxamide is administered as 100 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 20 mg dosages (which can be in capsules or tablets) given for 5 consecutive days and repeated every 28 days. The maintenance phase in Example 3I can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3J: N-(4-{[6,7-bis(methyloxy)quinolin-4-yl]oxy}phenyl)-N'-(4-fluorophenyl)cyclopropane-1,1-dicarboxamide is administered as 25 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 100 mg dosages (which can be in capsules or tablets) given for 5 consecutive days and repeated every 28 days. The maintenance phase in Example 3J can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3K: N-(4-{[6,7-bis(methyloxy)quinolin-4-yl]oxy}phenyl)-N'-(4-fluorophenyl)cyclopropane-1,1-dicarboxamide is administered as 50 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 100 mg dosages (which can be in capsules or tablets) given for 5 consecutive days and repeated every 28 days. The maintenance phase in Example 3K can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3L: N-(4-{[6,7-bis(methyloxy)quinolin-4-yl]oxy}phenyl)-N'-(4-fluorophenyl)cyclopropane-1,1-dicarboxamide is administered as 75 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 100 mg dosages (which can be in capsules or tablets) given for 5 consecutive days and repeated every 28 days. The maintenance phase in Example 3L can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3M: N-(4-{[6,7-bis(methyloxy)quinolin-4-yl]oxy}phenyl)-N'-(4-fluorophenyl)cyclopropane-1,1-dicarboxamide is administered as 100 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 100 mg dosages (which can be in capsules or tablets) given for 5 consecutive days and repeated every 28 days. The maintenance phase in Example 3M can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3N: N-(4-{[6,7-bis(methyloxy)quinolin-4-yl]oxy}phenyl)-N'-(4-fluorophenyl)cycloparte-1,1-dicarboxamide is administered as 25 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 140 mg dosages (which can be in capsules or tablets) given for 5 consecutive days and repeated every 28 days. The maintenance phase in Example 3N can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3O: N-(4-{[6,7-bis(methyloxy)quinolin-4-yl]oxy}phenyl)-N'-(4-fluorophenyl)cyclopropane-1,1-dicarboxamide is administered as 50 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 140 mg dosages (which can be in capsules or tablets) given for 5 consecutive days and repeated every 28 days. The maintenance phase in Example 3O can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3P: N-(4-{[6,7-bis(methyloxy)quinolin-4-yl]oxy}phenyl)-N'-(4-fluorophenyl)cyclopropane-1,1-dicarboxamide is administered as 75 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 140 mg dosages (which can be in capsules or tablets) given for 5 consecutive days and repeated every 28 days. The maintenance phase in Example 3P can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3Q: N-(4-{[6,7-bis(methyloxy)quinolin-4-yl]oxy}phenyl)-N'-(4-fluorophenyl)cyclopropane-1,1-dicarboxamide is administered as 100 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 140 mg dosages (which can be in capsules or tablets) given for 5 consecutive days and repeated every 28 days. The maintenance phase in Example 3Q can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3R: N-(4-{[6,7-bis(methyloxy)quinolin-4-yl]oxy}phenyl)-N'-(4-fluorophenyl)cyclopropane-1,1-dicarboxamide is administered as 25 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N-(4-fluorophenyl)cyclopropane-1,1-dicarboxamide is administered as a single oral agent supplied as 25 mg and 100 mg dosages (which can be in capsules or tablets). TMZ, when given, is supplied as 180 mg dosages (which can be in capsules or tablets) given for 5 consecutive days and repeated every 28 days. The maintenance phase in Example 3R can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3S: N-(4-{[6,7-bis(methyloxy)quinolin-4-yl]oxy}phenyl)-N'-(4-fluorophenyl)cyclopropane-1,1-dicarboxamide is administered as 50 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 180 mg dosages (which can be in capsules or tablets) given for 5 consecutive days and repeated every 28 days. The maintenance phase in Example 3S can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3T: N-(4-{[6,7-bis(methyloxy)quinolin-4-yl]oxy}phenyl)-N'-(4-fluorophenyl)cyclopropane-1,1-dicarboxamide is administered as 75 mg dosages (which can be in a capsule or tablet). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 180 mg dosages (which can be in capsules or tablets) given for 5 consecutive days and repeated every 28 days. The maintenance phase in Example 3T can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3U: N-(4-{[6,7-bis(methyloxy)quinolin-4-yl]oxy}phenyl)-N'-(4-fluorophenyl)cyclopropane-1,1-dicarboxamide is administered as 100 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 180 mg dosages (which can be in capsules or tablets) given for 5 consecutive days and repeated every 28 days. The maintenance phase in Example 3U can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3V: N-(4-{[6,7-bis(methyloxy)quinolin-4-yl]oxy}phenyl)-N'-(4-fluorophenyl)cyclopropane-1,1-dicarboxamide is administered as 25 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied in doses of 200 mg/m$^2$/day given for 5 consecutive days and repeated every 28 days. The maintenance phase in Example 3V can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3W: N-(4-{[6,7-bis(methyloxy)quinolin-4-yl]oxy}phenyl)-N'-(4-fluorophenyl)cyclopropane-1,1-dicarboxamide is administered as 50 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied in doses of 200 mg/m$^2$/day given for 5 consecutive days and repeated every 28 days. The maintenance phase in Example 3W can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3X: N-(4-{[6,7-bis(methyloxy)quinolin-4-yl]oxy}phenyl)-N'-(4-fluorophenyl)cyclopropane-1,1-dicarboxamide is administered as 75 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied in doses of 200 mg/m$^2$/day given for 5 consecutive days and repeated every 28 days. The maintenance phase in Example 3X can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3Y: N-(4-{[6,7-bis(methyloxy)quinolin-4-yl]oxy}phenyl)-N'-(4-fluorophenyl)cyclopropane-1,1-dicarboxamide is administered as 100 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied in doses of 200 mg/m$^2$/day given for 5 consecutive days and repeated every 28 days. The maintenance phase in Example 3Y can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3Z: N-(4-{[6,7-bis(methyloxy)quinolin-4-yl]oxy}phenyl)-N'-(4-fluorophenyl)cyclopropane-1,1-dicarboxamide is administered as 25 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 250 mg dosages (which can be in capsules or tablets) given for 5 consecutive days and repeated every 28 days. The maintenance phase in Example 3Z can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3AA: N-(4-{[6,7-bis(methyloxy)quinolin-4-yl]oxy}phenyl)-N'-(4-fluorophenyl)cyclopropane-1,1-dicarboxamide is administered as 50 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 250 mg dosages (which can be in capsules or tablets) given for 5 consecutive days and repeated every 28 days. The maintenance phase in Example 3AA can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3AB: N-(4-{[6,7-bis(methyloxy)quinolin-4-yl]oxy}phenyl)-N'-(4-fluorophenyl)cyclopropane-1,1-dicarboxamide is administered as 75 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied in doses of 200 mg/m$^2$/day given for 5 consecutive days and repeated every 28 days. The maintenance phase in Example 3AB can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

Example 3AC: N-(4-{[6,7-bis(methyloxy)quinolin-4-yl]oxy}phenyl)-N'-(4-fluorophenyl)cyclopropane-1,1-dicarboxamide is administered as 100 mg dosages (which can be in capsules or tablets). Some patients that have a mutation in the MGMT promoter, wherein the mutated MGMT promoter is an unmethylated promoter, may not receive TMZ and instead receive N-(4-{[6,7-bis(methyloxy)quinolin-4-yl]oxy}phenyl)-N'-(4-fluorophenyl)cyclopropane-1,1-dicarboxamide as a single agent in combination with RT. N-(4-{[6,7-bis(methyloxy)quinolin-4-yl]oxy}phenyl)-N'-(4-fluorophenyl)cyclopropane-1,1-dicarboxamide is administered as a single oral agent supplied as 25 mg and 100 mg dosages (which can be in capsules or tablets). TMZ, when given, is supplied as 250 mg dosages (which can be in capsules or tablets) given for 5 consecutive days and repeated every 28 days. The maintenance phase in Example 3AC can be combined with the concurrent phase of any of Examples 2A, 2B, 2C, 2D, 2E, 2F, 2G, 2H, 2I, 2J, 2K, 2L, 2M, 2N, 2O, 2P, 2Q, 2R, 2S, 2T, 2U, 2V, 2W, 2X, 2Y, 2Z, 2AA, 2AB, 2AC and 2AD.

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A process for preparing N-(4-{[6,7-bis(methyloxy)quinolin-4-yl]oxy}phenyl)-M-(4-fluorophenyl)cyclopropane-1,1-dicarboxamide:

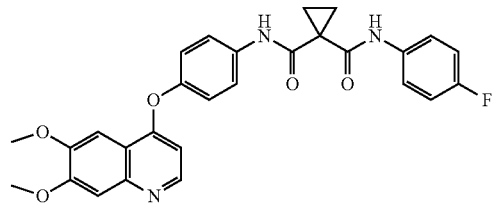 [SMILES: COc1cc2nccc(Oc3ccc(NC(=O)C4(C(=O)Nc5ccc(F)cc5)CC4)cc3)c2cc1OC]

comprising the steps of:
(a) reacting

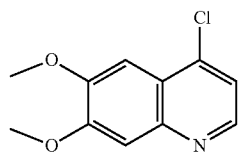

with
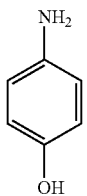
in the presence of sodium t-butoxide to provide
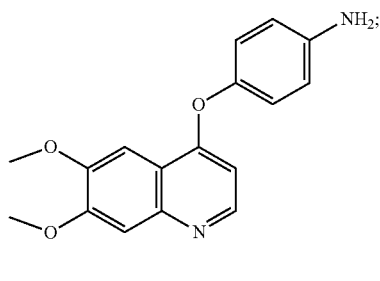 [SMILES: COc1cc2nccc(Oc3ccc(N)cc3)c2cc1OC]
and
(b) reacting
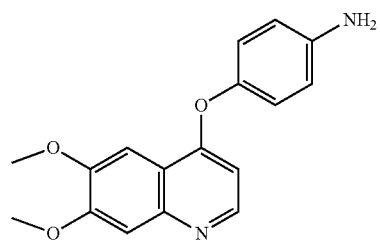 [SMILES: COc1cc2nccc(Oc3ccc(N)cc3)c2cc1OC]
with
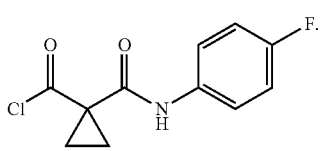 [SMILES: O=C(Cl)C1(C(=O)Nc2ccc(F)cc2)CC1]
2. The process of claim 1, wherein compound
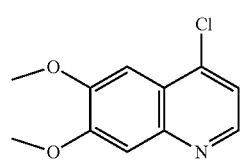
is prepared by reacting
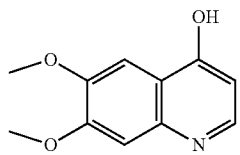
with POCl₃.
3. A process for preparing N-(4-{[6,7-bis(methyloxy) quinolin-4-yl]oxy}phenyl)-N'-(4-fluorophenyl)cyclopropane-1,1-dicarboxamide
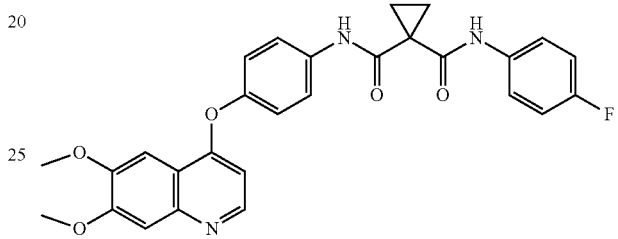
comprising the steps of:
(a) reacting
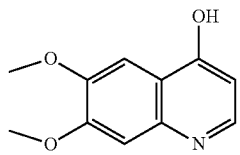
with POCl₃ to provide
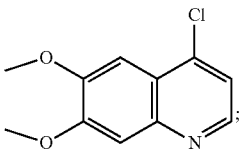
(b) reacting
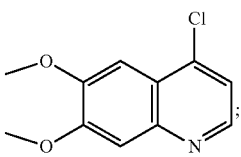

with
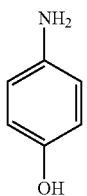
in the presence of sodium t-butoxide to provide
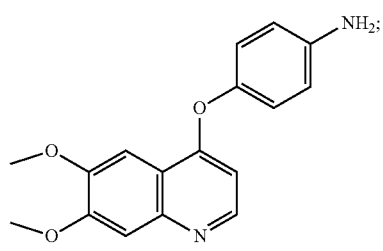 [SMILES: COc1cc2nccc(Oc3ccc(N)cc3)c2cc1OC]
and
(c) reacting
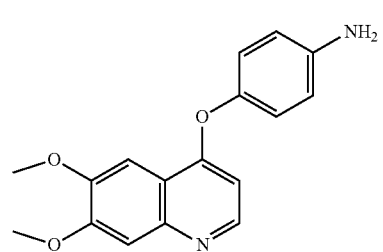 [SMILES: COc1cc2nccc(Oc3ccc(N)cc3)c2cc1OC]
with
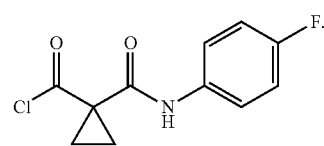 [SMILES: O=C(Cl)C1(C(=O)Nc2ccc(F)cc2)CC1]
4. A process for preparing N-(4-{[6,7-bis(methyloxy) quinolin-4-yl]oxy}phenyl)-N'-(4-fluorophenyl)cyclopropane-1,1-dicarboxamide, L-malate
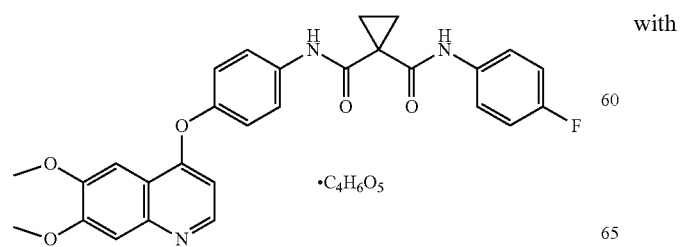
comprising the steps of:
(a) reacting
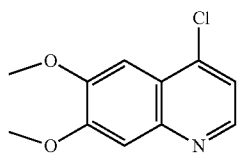
with
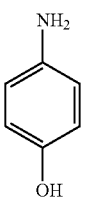
in the presence of sodium t-butoxide to provide
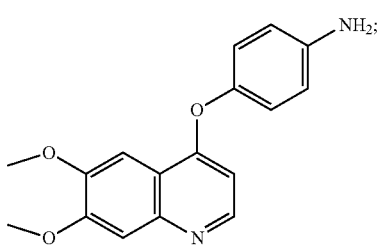 [SMILES: COc1cc2nccc(Oc3ccc(N)cc3)c2cc1OC]
and
(b) reacting
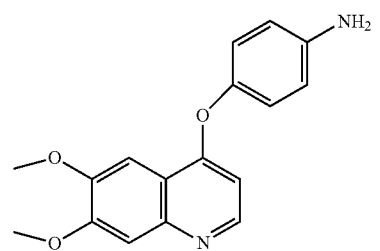 [SMILES: COc1cc2nccc(Oc3ccc(N)cc3)c2cc1OC]
with
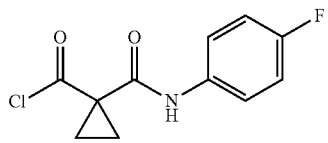 [SMILES: O=C(Cl)C1(C(=O)Nc2ccc(F)cc2)CC1]

to provide
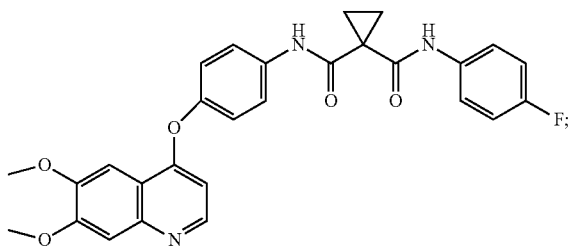 [SMILES: COc1cc2nccc(Oc3ccc(NC(=O)C4(C(=O)Nc5ccc(F)cc5)CC4)cc3)c2cc1OC]
and
(c) reacting
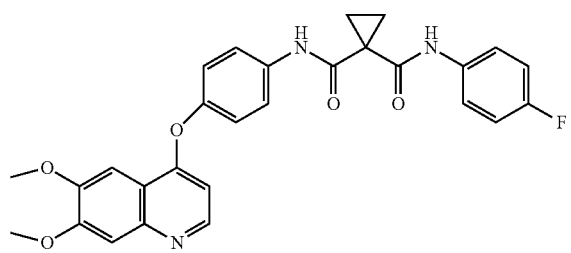 [SMILES: COc1cc2nccc(Oc3ccc(NC(=O)C4(C(=O)Nc5ccc(F)cc5)CC4)cc3)c2cc1OC]
with L-malic acid.
5. The process of claim 4, wherein compound
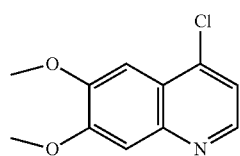
is prepared by reacting
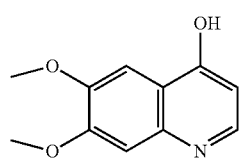
with POCl₃.
6. A process for preparing N-(4-{[6,7-bis(methyloxy)quinolin-4-yl]oxy}phenyl)-N'-(4-fluorophenyl)cyclopropane-1,1-dicarboxamide, L-malate
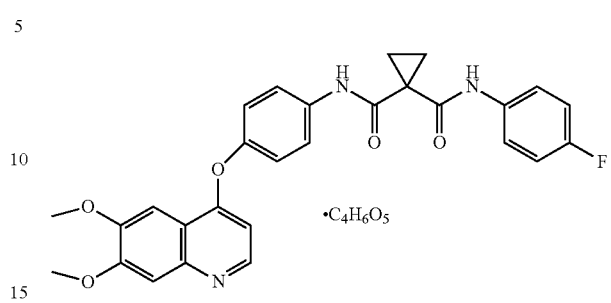
comprising the steps of:
(a) reacting
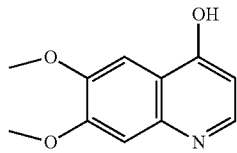
with POCl₃ to provide
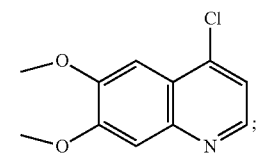
(b) reacting
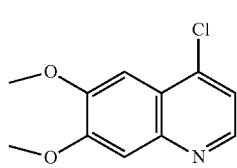
with
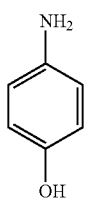

in the presence of sodium t-butoxide to provide
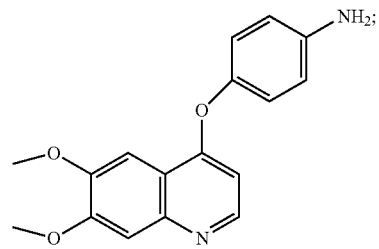 [SMILES: COc1cc2nccc(Oc3ccc(N)cc3)c2cc1OC]
and
(c) reacting
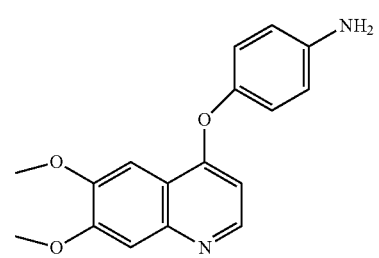 [SMILES: COc1cc2nccc(Oc3ccc(N)cc3)c2cc1OC]
with
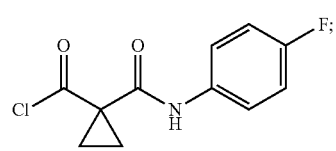 [SMILES: O=C(Cl)C1(C(=O)Nc2ccc(F)cc2)CC1]
and
(d) reacting
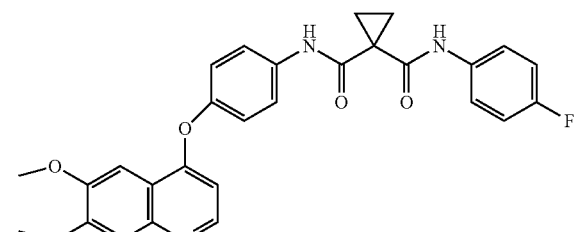
with L-malic acid.
* * * * *